US00PP17602P2

(12) United States Plant Patent
Smith

(10) Patent No.: US PP17,602 P2
(45) Date of Patent: Apr. 17, 2007

(54) ***HIBISCUS* PLANT NAMED 'CARAFE YOCHABLIS'**

(50) Latin Name: *Hibiscus moscheutos*
Varietal Denomination: Carafe Yochablis

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 22 days.

(21) Appl. No.: 11/177,877

(22) Filed: Jul. 8, 2005

(51) Int. Cl.
*A01H 5/00* (2006.01)

(52) U.S. Cl. ..... Plt./257

(58) Field of Classification Search ..... Plt./257
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct *Hibiscus* plant named 'Carafe Yochablis', characterized by its upright and somewhat outwardly spreading plant habit; freely branching and vigorous growth habit; early flowering habit; large white single flowers blushed with pink towards the center and occasionally towards the margins; and excellent garden performance.

2 Drawing Sheets

Botanical designation: *Hibiscus moscheutos.*
Cultivar denomination: 'Carafe Yochablis'.

CROSS-REFERENCE TO RELATED APPLICATIONS

*Hibiscus* Plant named 'Carafe Yobordeaux'; Mark A. Smith, applicant; disclosed in a U.S. Plant patent application filed concurrently.

BACKGROUND OF THE INVENTION

The present invention relates to a new and distinct cultivar of *Hibiscus,* botanically known as *Hibiscus moscheutos,* and hereinafter referred to by the name 'Carafe Yochablis'.

The new *Hibiscus* is a product of a planned breeding program conducted by the Inventor in Alva, Fla. The objective of the breeding program is to create new freely-branching and *Hibiscus* cultivars with a compact plant habit and attractive flower coloration.

The new *Hibiscus* originated from a self-pollination made by the Inventor in Alva, Fla. during the summer of 2001 of the *Hibiscus moscheutos* cultivar Carafe Yobordeaux, disclosed in a U.S. Plant patent application Ser. No. 11/178,272. The cultivar Carafe Yochablis was discovered and selected by the Inventor as a flowering plant within the progeny of the stated self-pollination in a controlled environment in Alva, Fla. in April, 2002.

Asexual reproduction of the new *Hibiscus* by vegetative terminal cuttings in a controlled environment in Alva, Fla. since May, 2002, has shown that the unique features of this new *Hibiscus* are stable and reproduced true to type in successive generations.

SUMMARY OF THE INVENTION

The cultivar Carafe Yochablis has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Carafe Yochablis'. These characteristics in combination distinguish 'Carafe Yochablis' as a new and distinct cultivar:

1. Upright and somewhat outwardly spreading plant habit.
2. Freely branching and vigorous growth habit.
3. Early flowering habit.
4. Large white single flowers blushed with pink towards the center and occasionally towards the margins.
5. Excellent garden performance.

Plants of the new *Hibiscus* can be compared to plants of the parent, the cultivar Carafe Yobordeaux. Plants of the new *Hibiscus* differ from plants of the cultivar Carafe Yobordeaux in the following characteristics:

1. Plants of the new *Hibiscus* flower about two days later than plants of the cultivar Carafe Yobordeaux.
2. Plants of the new *Hibiscus* and the cultivar Carafe Yobordeaux differ in flower coloration as plants of the cultivar Carafe Yobordeaux have red-colored flowers.

Plants of the new *Hibiscus* can be compared to plants of the *Hibiscus* cultivar Blue River II, not patented. In side-by-side comparisons conducted in Alva, Fla., plants of the new *Hibiscus* differed from plants of the cultivar Blue River II in the following characteristics:

1. Plants of the new *Hibiscus* were shorter, fuller and stronger than plants of the cultivar Blue River II.
2. Plants of the new *Hibiscus* and the cultivar Blue River II differed in flower color as plants of the cultivar Blue River II had pure white-colored flowers.

Plants of the new *Hibiscus* can also be compared to plants of the Hibiscus cultivar Disco Belle White, not patented. In side-by-side comparisons conducted in Alva, Fla., plants of the new *Hibiscus* differed from plants of the cultivar Disco Belle White in the following characteristics:

1. Plants of the new *Hibiscus* were taller and fuller than plants of the cultivar Disco Belle White.

2. Plants of the new *Hibiscus* flowered about three days later than plants of the cultivar Disco Belle White.
3. Plants of the new *Hibiscus* had larger flowers than plants of the cultivar Disco Belle White.
4. Plants of the new *Hibiscus* and the cultivar Disco Belle White differed in flower color as plants of the cultivar Disco Belle White had white-colored flowers with distinct red purple-colored centers.

BRIEF DESCRIPTION OF THE PHOTOGRAPHS

The accompanying colored photographs illustrate the overall appearance of the new *Hibiscus,* showing the colors as true as it is reasonably possible to obtain in colored reproductions of this type. Colors in the photographs may differ slightly from the color values cited in the detailed botanical description which accurately describe the colors of the new *Hibiscus*.

The photograph on the first sheet comprises a side perspective view of a typical flowering plant of 'Carafe Yochablis' grown in an outdoor nursery in Alva, Fla. for about six months.

The photograph on the second sheet comprises a close-up view of a typical flower of 'Carafe Yochablis'.

DETAILED BOTANICAL DESCRIPTION

The following observations, measurements and values describe plants grown in Alva, Fla. in one-gallon containers in a polypropylene-covered shadehouse during the summer and under conditions which closely approximate commercial production. During the production of the plants, day temperatures ranged from 29° C. to 32° C. and night temperatures ranged from 21° C. to 24° C. Plants were pinched about one month after planting. The description was taken about two months after the pinch. In the description, color references are made to The Royal Horticultural Society Colour Chart, 1995 Edition, except where general terms of ordinary dictionary significance are used.

Botanical classification: *Hibiscus moscheutos* cultivar Carafe Yochablis.

Parentage: Self-pollination of *Hibiscus moscheutos* cultivar Carafe Yobordeaux, disclosed in a U.S. Plant patent application filed concurrently.

Propagation:

*Type.*—By vegetative terminal cuttings.

*Time to initiate roots, summer.*—About eight days at temperatures of 30° C.

*Time to initiate roots, winter.*—About ten days at temperatures of 21° C.

*Time to develop roots, summer.*—About 12 to 14 days at temperatures of 30° C.

*Time to develop roots, winter.*—About 18 to 21 days at temperatures of 21° C.

*Root description.*—Thick, fibrous; white in color.

*Rooting habit.*—Freely branching.

Plant description:

*Plant form and growth habit.*—Perennial shrub; upright and somewhat outwardly spreading plant habit. Vigorous growth habit.

*Branching habit.*—Freely branching, lateral branches potentially forming at every node.

*Plant height.*—About 49 cm.

*Plant diameter* (*area of spread*).—About 42.5 cm.

*Lateral branch description.*—Length: About 33 cm. Diameter: About 7.5 mm. Internode length: About 2.7 cm. Texture: Smooth, glabrous. Color: 146A.

*Foliage description.*—Arrangement: Alternate, simple. Length: About 10.2 cm. Width: About 8.1 cm. Shape: Cordate to ovate. Apex: Acute; narrowly tapering. Base: Cordate. Margin: Crenate; slightly undulate. Texture, upper and lower surfaces: Smooth, glabrous. Venation pattern: Palmate. Color: Developing and fully expanded foliage, upper surface: Darker green than 147A. Developing and fully expanded foliage, lower surface: Close to 147B. Venation, upper surface: Close to 147A; towards the base, close to 187A. Venation, lower surface: 144A to 144B. Petiole: Length: About 3.4 cm. Diameter: About 3 mm. Texture, upper and lower surfaces: Smooth, glabrous. Color, upper and lower surfaces: 146A to 146B.

Flower description:

*Flower arrangement.*—Flowers develop at axillary leaf axils; typically one or two flowers per axil. Flowers face upright to outward.

*Flower appearance.*—Rotate white-colored flowers blushed with pink towards the center and occasionally towards the margins. Flowers are open for about two days. Flowers persistent.

*Natural flowering season.*—Usually spring and summer or during periods of warm weather.

*Flower diameter.*—About 12.5 cm.

*Flower length* (*height*).—About 2.7 cm.

*Flower bud.*—Length: About 1.6 cm. Diameter: About 1.5 cm. Shape: Ovoid. Color: Close to 147B.

*Petals.*—Quantity/arrangement: Corolla consists of five petals; petals imbricate. Length: About 6.3 cm. Width: About 6.8 cm. Shape: Roughly orbicular. Apex: Rounded; undulate. Base: Attenuate. Margin: Entire; undulate. Texture, upper and lower surfaces: Smooth, glabrous; satiny; rugose. Color: When opening, upper surface: Close to 155D; slightly overlain with 59A towards the base and occasionally towards the margins. When opening, lower surface: Close to 155D; slightly underlain with 59A towards the base and occasionally towards the margins. Fully opened, upper surface: Close to 155D; slightly overlain with 64A towards the base and occasionally towards the margins. Fully opened, lower surface: Close to 155D; slightly underlain with 64A towards the base and occasionally towards the margins.

*Sepals.*—Quantity/arrangement: Five sepals fused into a tubular calyx. Length: About 1.9 cm. Width: About 1.4 cm. Shape: Oblong. Apex: Cuspidate. Margin: Entire. Texture, upper surface: Smooth, glabrous. Texture, lower surface: Slightly pubescent. Color, upper surface: 146B. Color, lower surface: 146A.

*Bracts.*—Quantity/arrangement: About twelve in a single whorl. Length: About 1.8 cm. Width: About 3.5 mm. Shape: Lanceolate. Apex: Sharply acute. Margin: Entire. Texture, upper and lower surfaces: Pubescent. Color, upper surface: Close to 146A. Color, lower surface: Close to 147A.

*Peduncles.*—Length: About 1.75 cm. Diameter: About 2 mm. Angle: Mostly straight. Strength: Strong, flexible. Texture: Smooth, glabrous. Color: Close to 146A.

*Reproductive organs.*—Androecium: Stamen quantity per flower: Numerous, about 100. Anther shape: Reniform. Anther size: About 2 mm by 1 mm. Anther color: Close to 4C to 4D. Amount of pollen: None observed. Gynoecium: Pistil quality per flower: One with five stigmas. Pistil length: About 3 cm. Style length: About 2.5 cm. Style color: Close to 155D. Stigma shape: Rounded. Stigma color: Close to 154A. Ovary color: Close to 144A.

*Seed/fruit.*—Seed and fruit production has not been observed.

Garden performance: Plants of the new *Hibiscus* have been observed to be tolerant to wind and rain and to have excellent garden performance.

Hardiness: Plants of the new *Hibiscus* have been observed to be hardy to USDA Zone 5.

High temperature tolerance: Plants of the new *Hibiscus* have been observed to tolerate temperatures of about 40° C.

Disease/pest resistance: Plants of the new *Hibiscus* have not been observed to be resistant to pathogens and pests common to *Hibiscus*.

It is claimed:

1. A new and distinct *Hibiscus* plant named 'Carafe Yochablis', as illustrated and described.

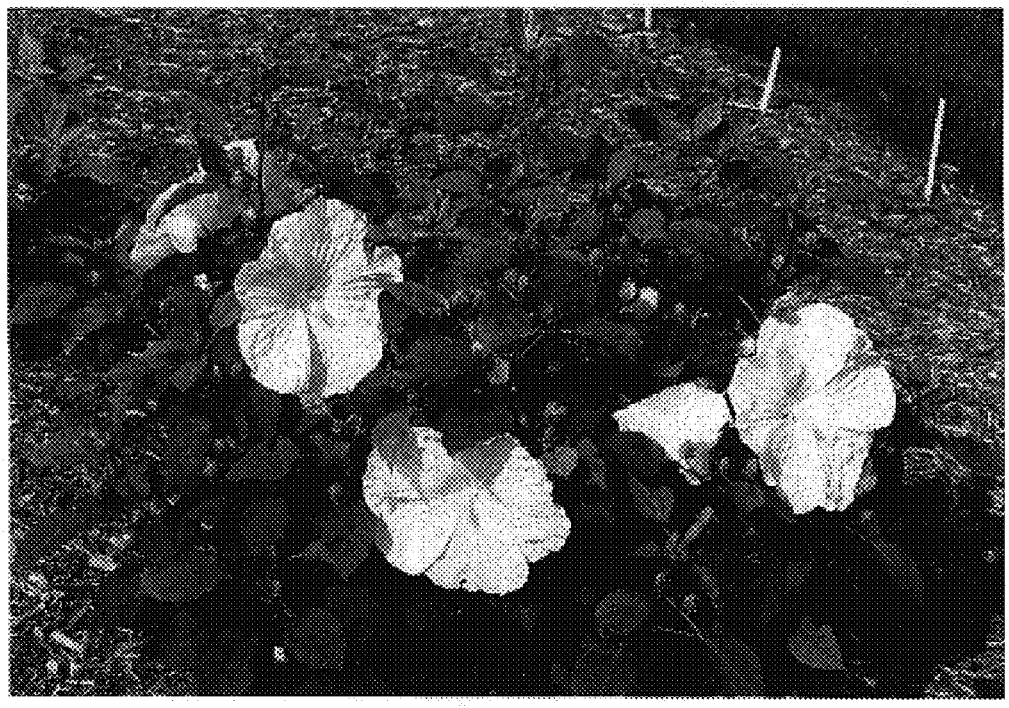

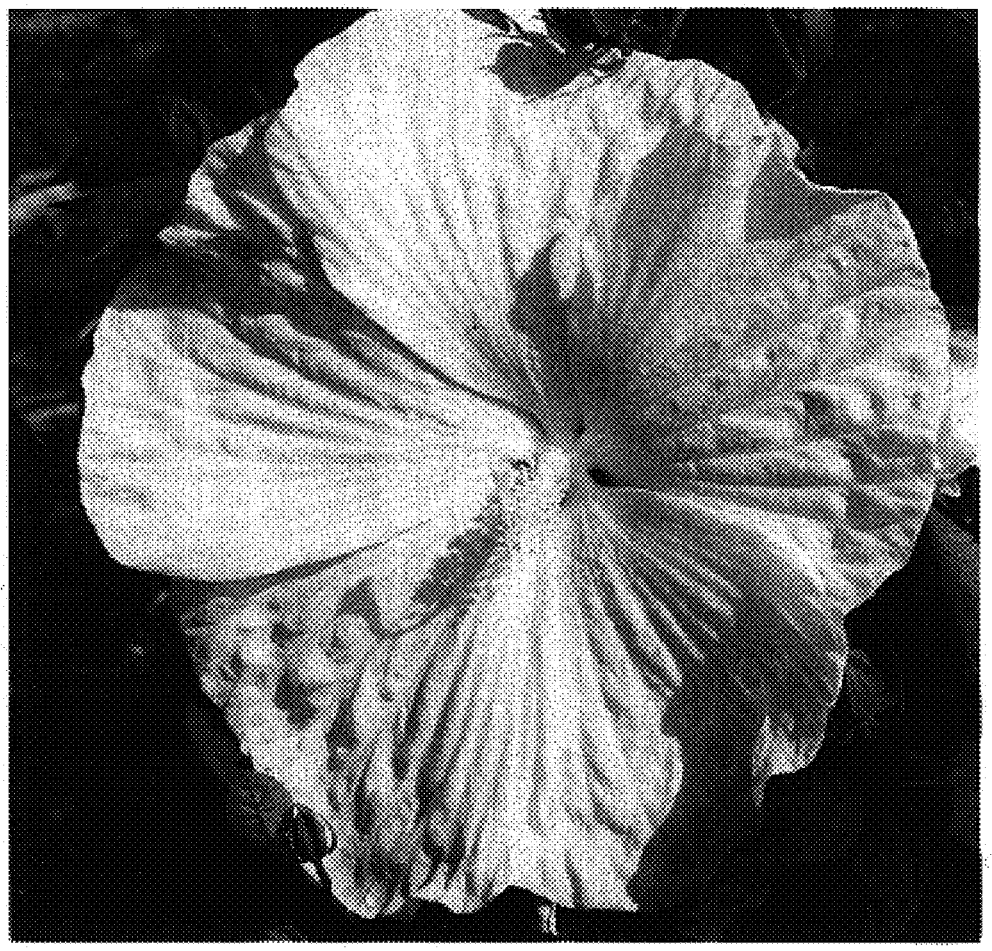

* * * * *